(12) United States Patent
Carter (10) Patent No.: US 7,300,406 B2
(45) Date of Patent: Nov. 27, 2007

(54) MEDICAL EXAMINATION APPARATUS

(76) Inventor: Vandette B. Carter, 5 Granada Crescent, White Plains, NY (US) 10603

(*) Notice: Subject to any disclaimer, the term of this patent is extended or adjusted under 35 U.S.C. 154(b) by 265 days.

(21) Appl. No.: 10/954,987

(22) Filed: Sep. 30, 2004

(65) Prior Publication Data

US 2005/0119584 A1    Jun. 2, 2005

Related U.S. Application Data (60) Provisional application No. 60/506,851, filed on Sep. 30, 2003.

(51) Int. Cl.
*A61B 7/04* (2006.01)
*A61B 5/0205* (2006.01)
*A61B 5/0404* (2006.01)

(52) U.S. Cl. .................... 600/528; 600/509; 381/67

(58) Field of Classification Search ........... 600/509, 600/528, 437; 181/131–137; D24/134; 381/67
See application file for complete search history.

(56) References Cited

U.S. PATENT DOCUMENTS

| | | | |
|---|---|---|---|
| 4,005,278 A * | 1/1977 | Gorike | 381/373 |
| 4,072,822 A | 2/1978 | Yamada | |
| 4,301,809 A * | 11/1981 | Pinchak | 600/508 |
| 4,362,164 A | 12/1982 | Little et al. | |
| 4,598,417 A | 7/1986 | Deno | |
| 4,776,426 A * | 10/1988 | Kazama | 181/131 |
| 4,792,145 A | 12/1988 | Eisenberg et al. | |
| 5,213,108 A | 5/1993 | Bredesen et al. | |
| 5,365,935 A | 11/1994 | Righter et al. | |
| 5,387,232 A * | 2/1995 | Trailer | 607/124 |
| 5,602,924 A | 2/1997 | Durand et al. | |
| 5,798,489 A * | 8/1998 | Gillio | 181/131 |
| 5,813,979 A | 9/1998 | Wolfer | |
| 5,945,641 A * | 8/1999 | Shieh | 181/131 |
| 5,960,089 A * | 9/1999 | Bouricius et al. | 381/67 |
| 6,002,777 A * | 12/1999 | Grasfield et al. | 381/67 |
| 6,083,156 A * | 7/2000 | Lisiecki | 600/301 |
| 6,149,602 A | 11/2000 | Arcelus | |
| 6,202,784 B1 * | 3/2001 | Alatriste | 181/131 |
| 6,210,344 B1 * | 4/2001 | Perin et al. | 600/528 |
| 6,248,064 B1 * | 6/2001 | Gopinathan et al. | 600/300 |

(Continued)

FOREIGN PATENT DOCUMENTS

JP    10-127626    5/1998

(Continued)

*Primary Examiner*—Kennedy J. Schaetzle
*Assistant Examiner*—Jessica L. Reidel
(74) *Attorney, Agent, or Firm*—David Aker (57) ABSTRACT

An apparatus to enable health care providers to perform a number of diagnostic procedures, including listening to the heart, obtaining electrocardiograms and sonograms. A pocket size instrument displays an EKG tracing on its screen simultaneously upon auscultation of the heart. The abdomen may also be investigated by displaying a sonogram. Wireless broadband technology may provide a closed circuit interface for real-time wireless transmission of acquired data. Examination requires none of a multiplicity of wires to untangle, bulky machines or a technician to be summoned. Regurgitation, heart size, ischemia and heart murmurs can all be evaluated by a visual and auditory methods.

27 Claims, 8 Drawing Sheets

U.S. PATENT DOCUMENTS

| | | |
|---|---|---|
| 6,533,736 B1 | 3/2003 | Moore |
| 6,603,995 B1 | 8/2003 | Carter |
| 6,748,260 B2 | 6/2004 | Au et al. |
| 6,757,392 B1 | 6/2004 | Granzotto et al. |
| 2001/0030077 A1 | 10/2001 | Watson |
| 2001/0041845 A1* | 11/2001 | Kim .......................... 600/528 |
| 2002/0071570 A1* | 6/2002 | Cohen et al. ................. 381/67 |
| 2003/0073915 A1 | 4/2003 | McLeod et al. |
| 2003/0083563 A1* | 5/2003 | Katsman et al. ............ 600/407 |
| 2004/0138575 A1 | 7/2004 | Ueyama |

FOREIGN PATENT DOCUMENTS

| | | | |
|---|---|---|---|
| WO | WO 97/01987 | * | 1/1997 |
| WO | WO 00/42903 | | 7/2000 |
| WO | WO 01/78604 | * | 10/2001 |

\* cited by examiner

MEDICAL EXAMINATION APPARATUS

This application claims priority under 35 U.S.C. §119(e) from U.S. Provisional Patent Application Ser. No. 60/506,851 filed on Sep. 30, 2003, which is incorporated herein by reference in its entirety.

BACKGROUND OF THE INVENTION

1. Field of the Invention

The present invention relates to apparatus that may be used to examine a living body. More particularly, it relates to apparatus that may be used for listening for body sounds and for receiving electrical signals from the body. It also relates to apparatus which have the capability of examining a body with ultrasound.

2. Prior Art

The stethoscope since its perfection in 1855 by a New York Physician, Dr. George Cammann, has remained relatively unchanged in the last two centuries. Not much has been done or modified from its basic design and function since then. The stethoscope as it is to date, is greatly limited by what it can do. In the examination of the heart, only sound can be appreciated. While helpful in certain limited clinical situation, sound tells the medical practitioner very little about the true characteristic of the heart, such as its conduction or electrical activities and its true physical state.

The general shape of the stethoscope underwent some minor improvements. However, what has remained constant for the past 150 years is the appearance. There is probably a good reason for this. Besides the white coat that is so symbolic of a doctor, it is the stethoscope instrument that easily identifies a health care professional. The stethoscope has been revered as a symbol of the medical profession and more specifically for the health care provider. In some ways, in terms of its symbolism, the shape of the stethoscope can be likened to the gavel a judge uses.

The entire book of Bates, which is the gold standard physical diagnostic book, stresses the fundamentals of acquiring good clinical skills using the traditional stethoscope. There are clinician that are presently being trained that will prefer the natural appreciation of detecting sound coming from the heart in its pure form, using the traditional method. To enhance this feature, two diaphragms have been used to channel natural heart sound to the right and left ear, respectively.

However, it is in the electrical activities of the heart that are most appropriate for detecting signs which tell the practitioner if a heart is healthy, or not. The practitioner searches for pathologies with respect to electrolytes disturbances, heart muscle damage and/or enlargement; conduction abnormalities (such as prolonged Q-T intervals); rate of the heart; rhythm, axis and more.

Due to their cumbersome nature (because of bulky machines, complex lead arrangements, or the need for a technician) of obtaining an ECG on the general population, one is not routinely done in common practice.

For the most part, an EKG is reserved for age specific population or for people with established or suspected cardiac illnesses. In both cases the study is usually formerly requested and time is the factor that most clinicians have to deal with.

Sonogram technology has been adapted to investigate all forms of pathologies within the abdomen and heart. In addition it has been used to access vascular diseases of the extremities such as deep vein thrombosis; which is a rather prevalent condition. As before with an EKG, the clinician is often at the mercy of the sonogram technician in obtaining, and in some cases interpreting sonogram data.

SUMMARY OF THE INVENTION

It is an object of the invention to incorporate technological advances while preserving the basic design and functionality of the traditional stethoscope.

It is another object of the invention to provide an apparatus for obtaining an EKG trace quickly and efficiently.

It is yet another object of the invention to provide an apparatus that avoids the need for a multiplicity of electrical leads that are difficult to manage, and may become tangled.

It is still another object of the invention to provide new configurations for EKG electrodes that may be used with the apparatus of the invention and with other apparatus.

These objects and others are achieved in accordance with the invention in an apparatus for determining a condition of a living body, comprising a first portion for acquiring acoustic signals from said body, said first potion having electrodes for acquiring electric signals from said body; a second portion comprising an elongate housing having conduits for conducting signals from said first portion; and a third portion comprising a headset for listening to said acoustic signals; wherein said third portion is removeably connectable to said second portion. The apparatus may further comprising a communication link between said second portion and said third portion for transferring said signals when said first portion is not connected to said second portion. The communication link is preferably a broadband communications link. It is preferably a wireless communication link.

The first portion may further comprise a display for providing a visual indication representative of at least one of said signals.

The apparatus may be in combination with an external display coupled to said apparatus with a broadband wireless real-time connection for data originating in said apparatus.

The first portion may further comprise an ultrasonic transducer usable for performing an ultrasonic examination of at least a portion of said body.

The apparatus may be in combination with an external display coupled to said apparatus with a broadband wireless real-time connection for data originating in said apparatus, said data being derived from at least one of a sonogram, and an electrocardiogram. The second portion is configured with an elongate cavity and at least one cover for covering said cavity. The cover may comprise at least one door swingably mounted to said second portion so that said at least one door swings away from said cavity to expose said cavity.

The apparatus may further comprise a plurality of cords extending from said second portion, said cords each having a bundle of wires, each wire being configured at its end for an electrode for acquiring an electrical signal from said body, said cords being capable of bending and folding so as to fit within said cavity. The cords and said wires may be configured to place said electrodes for receiving EKG signals. The plurality may include two cords, a first of said cords being configured so that respective electrodes associated with said first cord receive signals from a first side of the body, and a second of said cords being configured so that respective electrodes associated with said second cord receive signals from a second side of the body. The first and second sides may be the left side and right side of said body.

The plurality may includes two cords, a first of said cords being configured so that respective electrodes associated with said first cord receive precordial signals from a body, and a second of said cords being configured so that respective electrodes associated with said second cord receive limb signals from the body.

The plurality may comprise three cords, a first of said cords having associated electrodes for receiving signals from both arms, a second of said cord having associated electrodes for receiving precordial signals, and a third one of said cords having associated electrodes for receiving signals from the both legs.

The first portion, the second portion and the third portion of the apparatus may each comprise at least one electrode for receiving electrical signals from said body. The apparatus may further comprise at least one adjustable light source on said first portion.

The first portion may comprise a diaphragm having a first part and a second part, and said headset may comprise a first earpiece and a second earpiece, said first part of said diaphragm providing signals for said first earpiece, and said second part of said diaphragm providing signals for said second earpiece.

The first portion may be releasably connected to said second portion, and said second portion may be releasably connected to and said third portion.

The invention is also directed to a method for obtaining an electrocardiogram, by using the apparatus as described herein. Further, the invention is directed to arrangements of leads for electrodes in respective cords, as also described herein.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENTS

Figure 1:
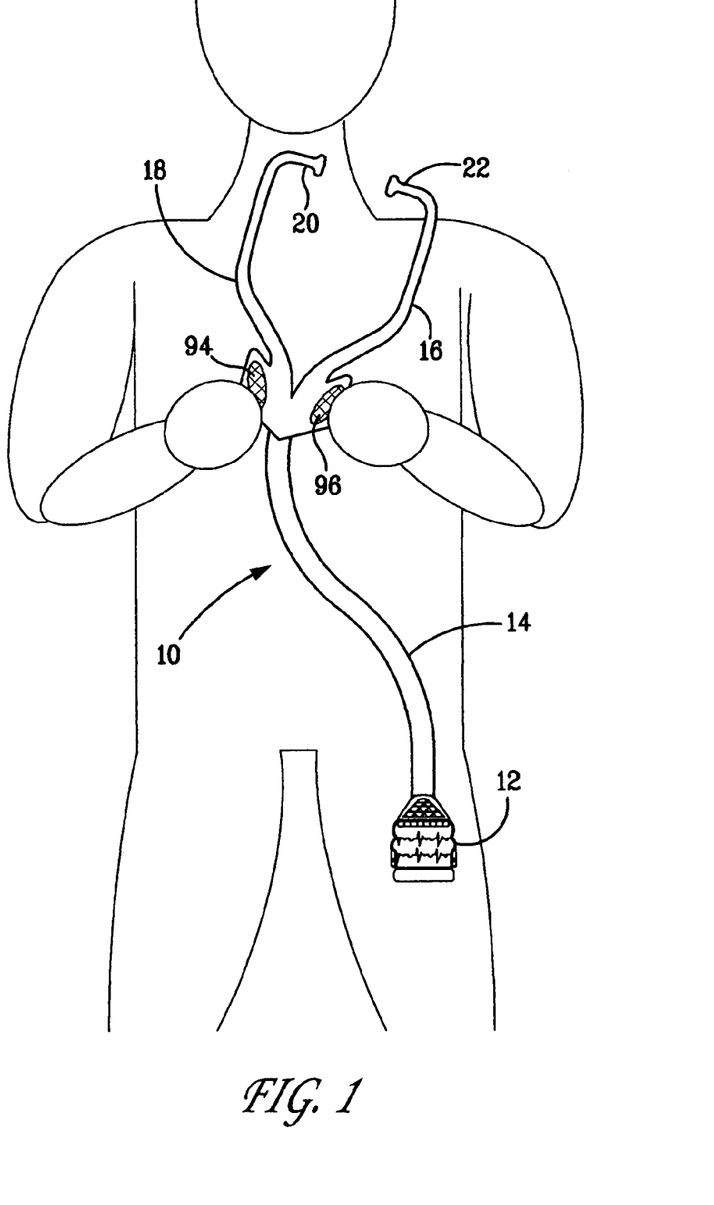
FIG. 1 is a plan view of an apparatus in accordance with the invention.

Referring to FIG. 1, there is shown a perspective view of an apparatus incorporating features of the present invention. Although the present invention will be described with reference to the embodiments shown in the drawings, it should be understood that the present invention can be embodied in many alternate forms of embodiments. In addition, any suitable size, shape or type of elements or materials could be used.

In FIG. 1, an apparatus shown generally as 10, in accordance with the invention is being held in the manner which illustrates the portions thereof, and will be discussed again below in terms of its use.

Apparatus 10 includes a first portion or head 12 which may be applied to a body to determine the condition thereof, a second portion which is an elongate body 14, and a third portion 16, which includes an earpiece assembly 18, which may be of a conventional type to the extent that has earpieces 20 and 22 for placement in the ears of a practitioner. Head 12 and third portion 16 may both be releasably coupled to body 14, thus providing a modular assembly, for ease of servicing and ease of use to for various purposes, as described below.

Figure 2:
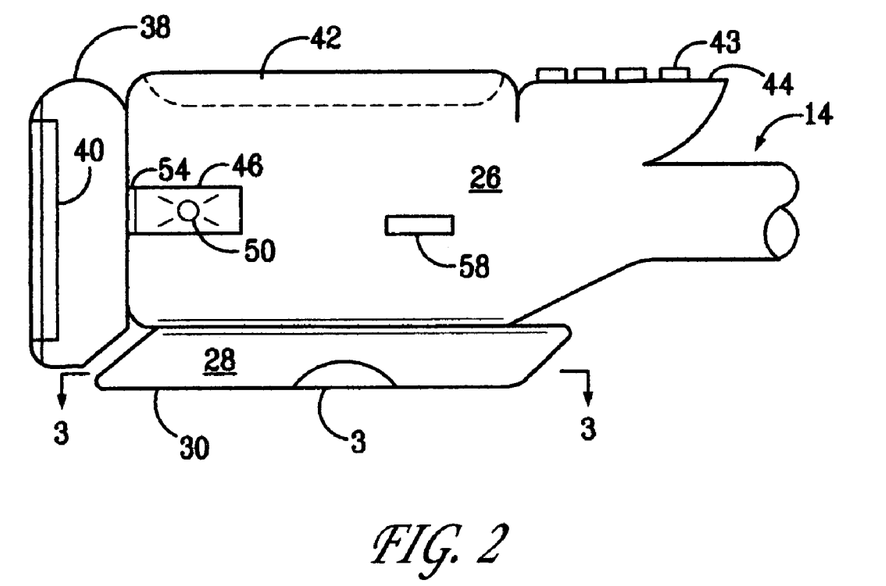
FIG. 2 is a slightly enlarged, side elevational view of a first portion of the apparatus shown of FIG. 1.

Referring to FIG. 2, head 12 has a housing 26 configured with an extension 28 that has on a planar underside, a diaphragm 30. Diaphragm 30 is constructed of suitable materials and in a suitable manner so as to have the acoustic properties of a conventional acoustic stethoscope diaphragm. However, diaphragm 30 may be configured with at least one or more electrodes for acquiring electrical signals from a living body undergoing examination.

Diaphragm 30 may be constructed as a split diaphragm, and appropriate arrangements may be provided so that one side of diaphragm 30 provides acoustic signals to one earpiece 20 and the other side of diaphragm 30 provides acoustic signals the other earpiece 22. These may be actual acoustic signals, or those provided by appropriate transducers, and amplification of electrical signals from those transducers.

Figure 3:
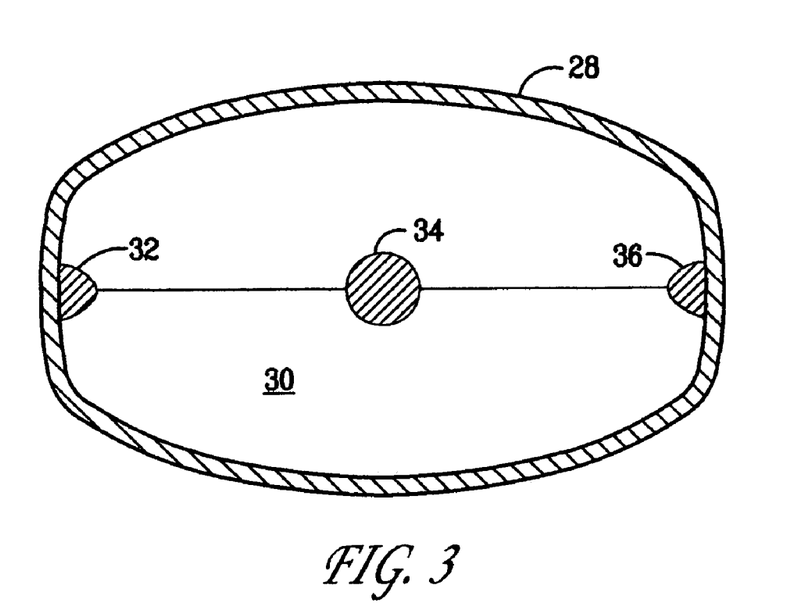
FIG. 3 is a cross-sectional view taken along line 3-3 of FIG. 2.

FIG. 3 shows that extension 28 of housing 26 need not be circular, and in fact may have a generally rectangular shape, although the sides of the rectangle may be curved. Diaphragm 30, secured about the periphery of the lower end of extension 28 of housing 26, may have a similar shape. Further, diaphragm 30 may have embedded therein a series of electrodes 32, 34 and 36 of the type discussed above. Alternatively, or in addition, there may be other vital sign sensors, such as blood oxygen or blood sugar monitoring sensors disposed on diaphragm 30 so that they can come into contact with, or at least acquire information from a patient when placed on the skin or in close proximity thereto.

Referring again to FIG. 2, a second housing extension 38 may house one or more ultrasonic transducer elements, as represented by 40. There may be a single transducer element, or an array of transducer elements, which are useful in ultrasonic diagnosis of conditions within the body. If an array is present, it may be electronically steered in a manner well known in the art.

A data display 42 is present at the top of housing 26 so as to be generally visible to the practitioner when apparatus 10 is in use for investigating any one of acoustic, electrical or ultrasound signals from a body. The display, and additional functions of apparatus 10 may be manipulated by use of keys 43 and/or touch screen regions or key pads 68 (also designated A, B, C, and D) on a keypad 44, also located on a top surface of housing 26, and as more fully described below with reference to FIG. 4.

Referring to both FIG. 2 and FIG. 3, housing 26 may have a lamp fixture 46 on one side, and 48 on the other. Thus, it is no longer necessary for clinicians to carry a separate penlight or flashlight to examine, for example, the mouth and throat of a patient. Lamp fixtures 46 and 48 may contain lamps 50 and 52, respectively, of different colors, or for example, one may provide a white light, while the other provides a green light by, for example, use of appropriate lamp covers or lenses 54 and 56, respectively. The lamps may be of the same type or of different types, and may include small incandescent lamps, light emitting diodes, or other lamps of a type well known in the art. Preferably, the lamps are chosen so that the amount of energy supplied to them can be varied to vary the intensity of the light produced. A control, such as a rheostat (not shown) operated by a dial 58 (FIG. 2) may be used to control the energy supplied. The control may be configured in the same manner as a conventional radio volume control, with an off position so as to turn off the lights and to save energy. While only one control is shown, it will be understood that separate controls may be provided on housing 26 for each of lamps 50 and 52.

Figure 4:
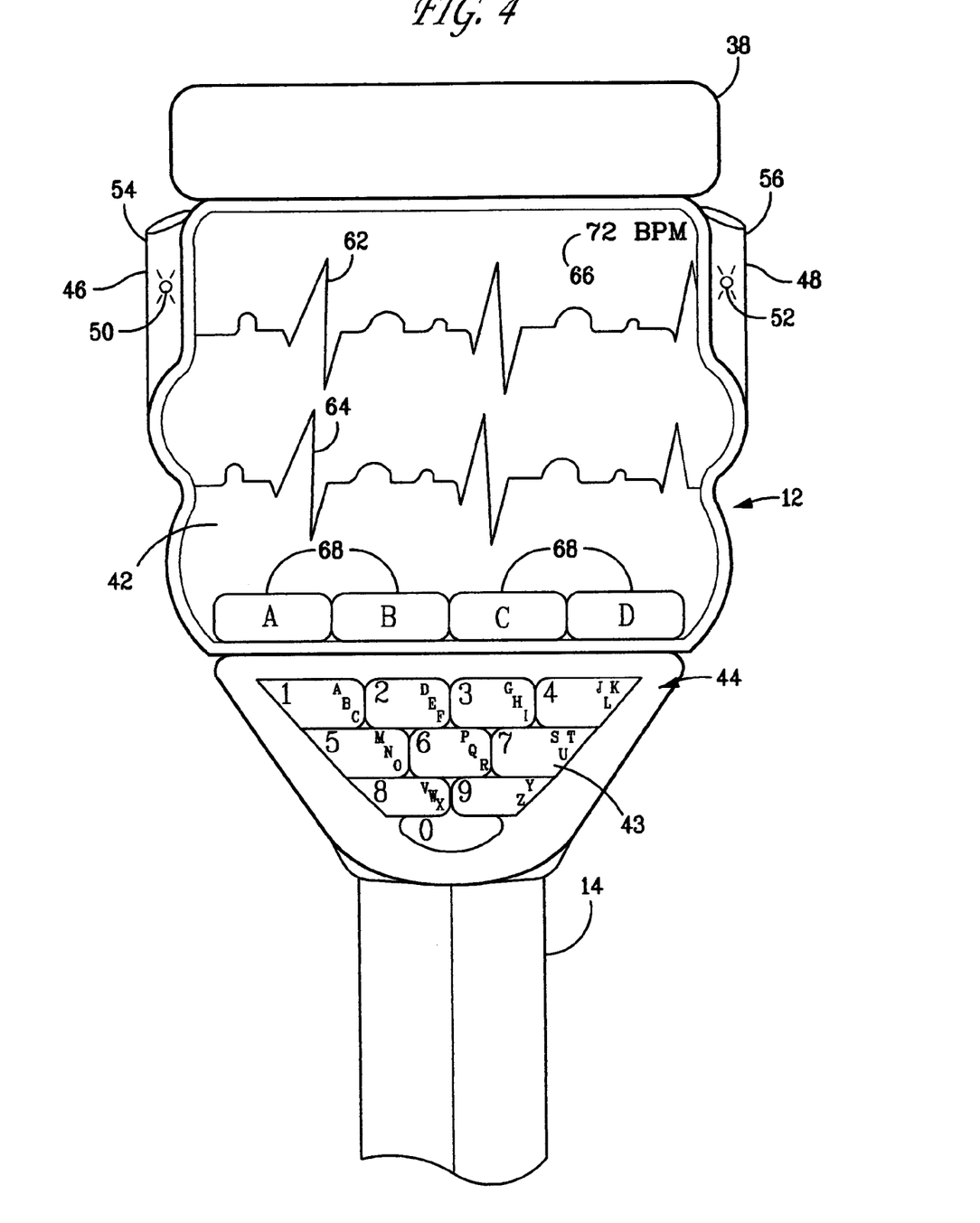
FIG. 4 is a slightly enlarged plan view of a first portion of the apparatus FIG. 1.

FIG. 4 shows that the display 42 may be used to provide waveform data display 62 and 64, such as EKG data from various electrodes as described above and as further described below. In addition, alphanumeric data of various kinds can be provided, such as, for example, heart rate, expressed in beats per minute (BPM), or blood sugar level, or blood oxygen level, depending on the types of vitals sensors associated with diaphragm 30, or placed elsewhere on apparatus 10, as more fully discussed below. Display 42 may include touch screen buttons for controlling the operation of the display or various other functions of apparatus 10, as an adjunct to keys 43 of keyboard 44. Display 10 is preferably a liquid crystal display, but various other display technologies presently known or yet to be developed, may also be used.

Figure 5:
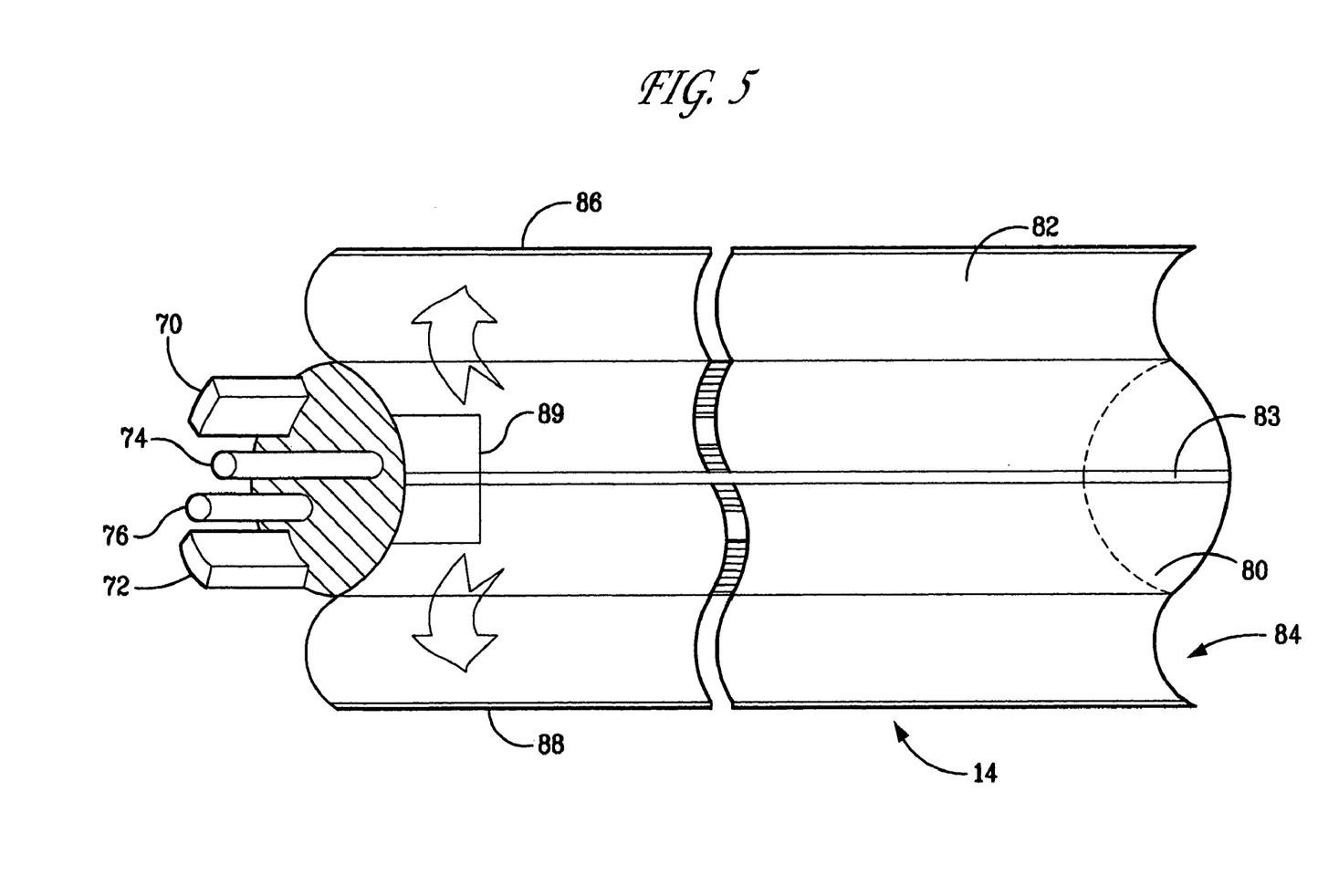
FIG. 5 is a partial plan view of a second portion of the apparatus of FIG. 1.

FIG. 5 illustrates details of the elongate body 14 to which head 12 is attached. While of a solid, generally filled structure, body 14 should be made of flexible materials to promote easy storage or carrying in a white coat pocket or around the neck of a clinician. Body 14 has at least two acoustic conduits 70 and 72 for conducting the acoustic signals received by diaphragm 30 to the earpieces 20 and 22 of earpiece assembly 18. Body 14 also has at least two electrical conductors 74 and 76, for conducting electrical signals from various electrodes of vital sign sensors, as more fully explained below. All of these projections from the end of body 14 may be received in correspondingly shaped openings in earpiece assembly 18, which is thus removeably attached to body 14. Body 14 is preferably formed with a cylindrical cavity 80, which may be used for storage, especially for storage of EKG leads or cords. Cavity 80 may be closed by one or two swinging doors 82 and 84, shown in their opened position so as to expose cavity 80, but which may close so that edges 86 and 88 meet along a line 83. Body 14 is also fitted with a communication module 89, for exchanging signals with the remainder of apparatus 10, especially when portion 16 is not attached to body 14.

Communication module 89 is conveniently fastened within cavity 80, such as to a wall thereof, to provide both protection and ease of access for servicing, should that become necessary. Communication module 89 should have facilities for data storage, which may be, for example, a flash memory of suitable size. Communication module 89 should also have the ability to send signal to a nearby display (for simultaneously display the image in a nearby terminal) or to a wireless network connection device via a broadband capability. Thus, the acquired data may be compiled to intelligently compare all of the twelve leads to investigate the heart's electrical activity, as more fully described below.

Figure 6:
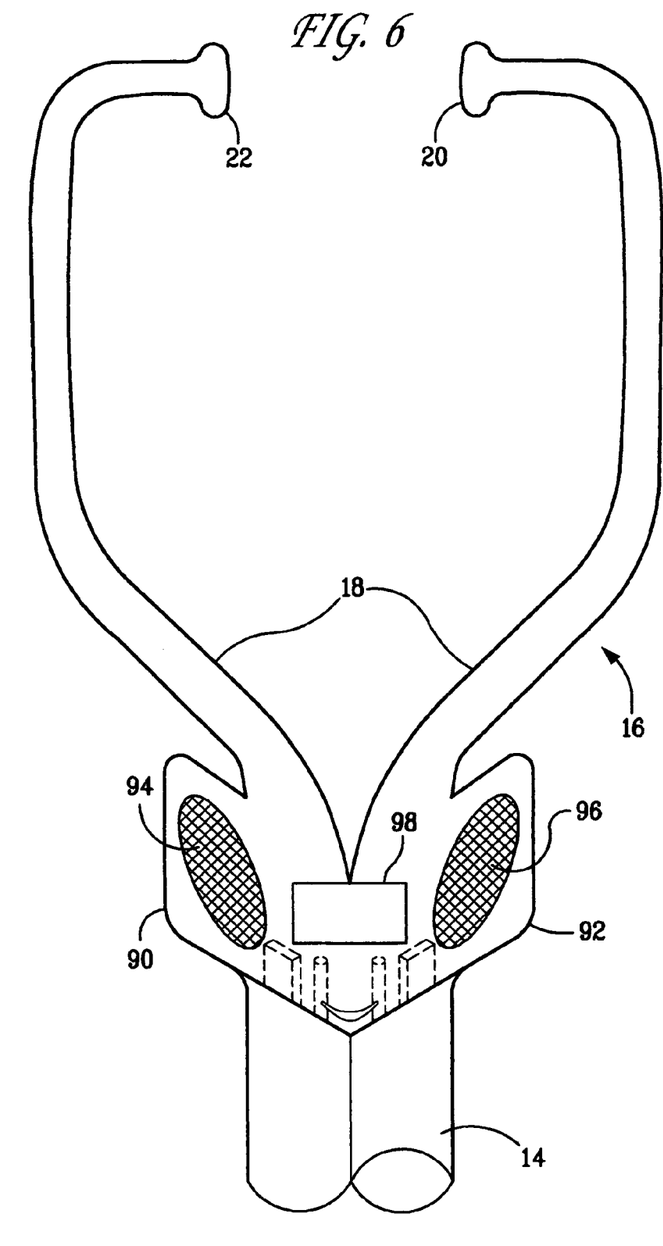
FIG. 6 is a bottom view of a third portion of the apparatus of FIG. 1.

FIG. 6 illustrates details of earpiece assembly 18. While earpiece assembly 18 may be similar to those of conventional construction in conducting acoustic signals to the ears, there are some additional unconventional features. Earpiece assembly 18 may be configured with housing extensions 90 and 92 having planar portions on which respective electrodes 94 and 96 are disposed. Electrodes 94 and 96 may be placed against the skin of a patient to receive EKG signals. Third portion 16 also may be configured with a communications module 98 to, for example, exchange data with communication module 89 of body 14. The communication link established between modules 89 and 98 may be a broadband wireless link. The link need only be active when portion 16 is separated from body 14, and may otherwise be shut down in response to sensing circuitry (not shown) associated with electrical conductors 74 and 76, in body 14, or with electrical contacts in portion 16 for making contact with electrical conductors 74 and 76, when received in opening in portion 16. The broadband communication link may also be activated on demand as when simultaneously viewing acquired data on a nearby monitor. The data can be sent simultaneously to a terminal within the vicinity for long-term storage, viewing and possibly for further processing.

Variations in placement of the components described above are possible. For example, housing extensions 90 and 92, having planar portions on which respective electrodes 94 and 96 are found may be a part of third portion 16, and thus permanently affixed thereto. In this case the distance between electrodes on diaphragm 30 and electrodes 94 and 96 could be varied, as long as body 14 is made of flexible materials, which is preferred, as discussed above.

Figure 7:
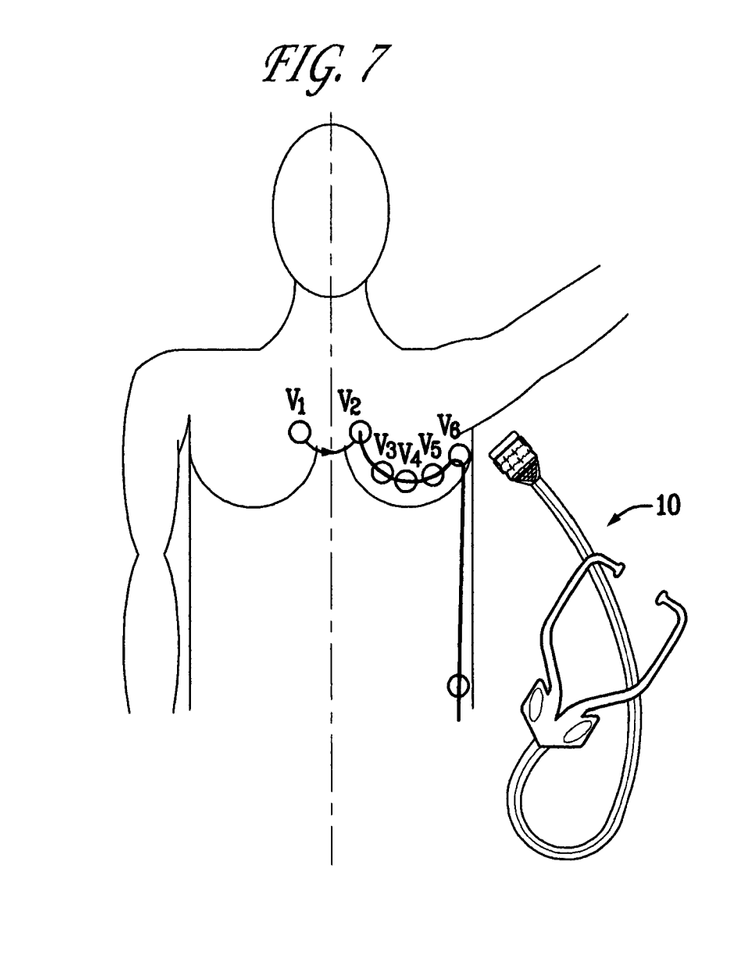
FIG. 7 illustrates the apparatus in accordance with the invention, and standard positions on a human for placement of EKG leads.

In a conventional twelve-lead electrocardiogram, six of the lead are termed "chest leads, "unipolar leads" or precordial leads. FIG. 7 shows the arrangement for the six chest components, which by using the apparatus in accordance with the invention, a clinician can obtain at the time of listening to the heart by following a predetermined path.

Referring again to FIG. 1, signals representative of the other half of the arrangement that makes up the full twelve-lead electrocardiogram (the "limb leads") may be acquired by using the apparatus of the invention. As illustrated FIG. 1, the patient is required to hold two of the electrodes 94 and 96 (RA and LA), while a third electrode, located on diaphragm 30 of apparatus 10 is positioned on the left leg (LL). In this basic arrangement, that conforms to the Einthoven's triangle to give the basic frame work to register the six limb leads (I, II, III aVF, aVR and aVL) that are generated in standardized methods, which are commonly used in existing EKG practice (with existing machines), are easily and conveniently generated with the apparatus in accordance with the invention.

Thus, there are three electrodes, namely: RA; LA and LL that are a permanent part of apparatus 10. As in FIG. 1, a physician can instruct a patient to hold two of the electrodes (RA and LA), while the third permanent electrode located on the diaphragm is placed on the patient's left leg—forming the Einthoven's Triangle. In this orientation, each of the six limb leads can be ascertained. This is a benefit of the apparatus in accordance with the invention in that it permits the clinician to non-invasively screen a patient's heart electrical activities, without the need for the patient to undress.

The arrangement that may be obtained using the techniques of FIG. 1 and FIG. 7 sequentially is comparable to that discussed in the literature as a screening mode. No additional accessories are required to obtain the full equivalent of a complete twelve lead EKG by using the arrangement in accordance with the invention. A simple two-step approach, with the brief cooperation of the patient to obtain the data, is all that is needed.

Thus, in this screening mode, all of the precordial or chest leads are acquired as the heart is auscultated along a choreographed ideal path on the chest wall using the diaphragm portion of the stethoscope. This information when gathered will correspond to the six leads "chest" component from a 12 leads EKG; they are $V_1$ through $V_6$. This process takes advantage of the fact that when listening to the heart to discriminate its sound, a pause is usually required, and this will provide enough time to simultaneously register an electric current originating from the heart. By sequentially positioning the diaphragms that features an electrode over the heart externally, readings that correspond to $V_1$-$V_6$ will be obtained. Also Leads I, II, and III, aVR, aVF and aVL can be determined as part of the screening mode evaluation process. This is obtained with the help of the patient who is instructed to touch two points on the stethoscope while a third part of the stethoscope is placed on the subject's left leg, thus creating an Einthoven triangle configuration on the test subject. These twelve (12) EKG tracings can be obtained without the usage of special external electrodes-such as silver chloride glues or stickers. A minor disadvantage is that a twelve lead EKG is obtained in two stages instead of one. This minor disadvantage is more than offset by the significant advantages discussed herein. In any event, the study is performed effortlessly with the participation of the test subject. It does not require a multitude of wires or connections or messy glues. It does not require a lengthy period of time to be done. It does not require that the patient undress. The difference is very marked and beneficial for the purpose of screening a patient.

Figure 8:
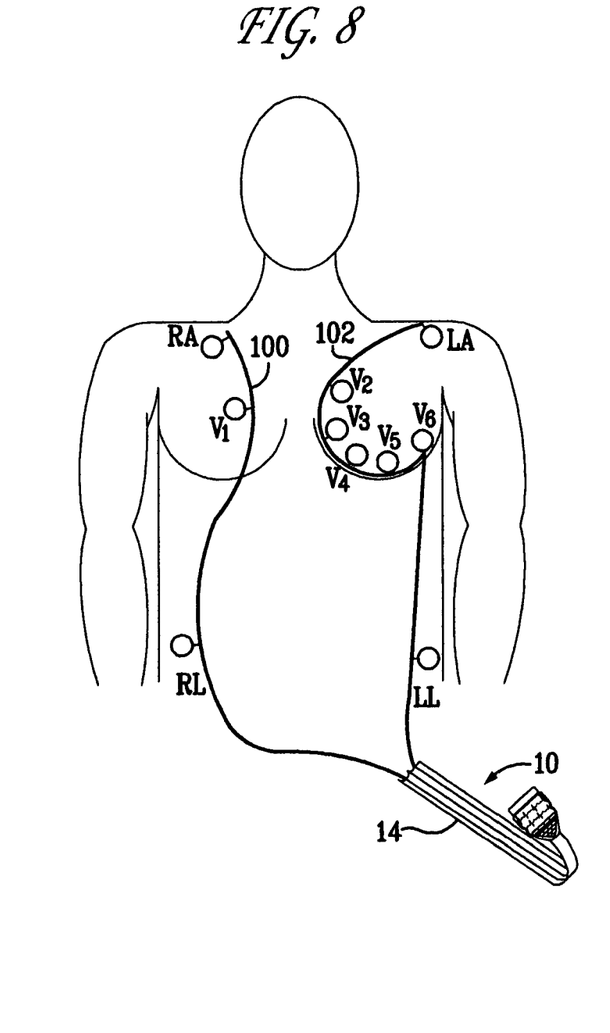
FIG. 8 illustrates use of the invention for monitoring twelve lead EKG activity in accordance with a first method in accordance with the invention.

FIG. 8 illustrates a new arrangement for the placement of the electrodes in accordance with the invention. In this configuration, only two cords are utilized, a first cord 100 for the right side of the body, and a second chord 102 for the left side of the body. Each cord 100 and 102 includes a bundle of insulated wires, each having an electrode at its end, with the wires leaving the bundle of wires at different points along the length of the cord respective cord 100 and 102. Thus each cord 100 and 102 has both precordial and limb electrodes. Thus, a shared/mixed system has been described with respect to the cords acquiring various leads. Specifically, cord 100 includes RA and V1 [which is a precordial lead] and RL bundled on the same branch). Cord 102 includes the remaining leads.

The cords 100 and 102 are advantageously stored in cavity 80 of body 14, until ready for use. The ends of the cords 100 and 102 not having electrodes are connected to wiring internal to apparatus 10 by passing through openings (not shown) in a wall or walls of cavity 80. Thus, doors 82 and 84 (FIG. 5) are opened to remove the cords for use, and after the procedure has been completed, and the cords 100 and 102 with their attached electrodes returned to cavity 80, the doors 82 and 84 are closed for convenient storage of the cords 100 and 102.

In a similar manner, it is possible to use a first cord with electrodes arranged at positions for receiving precordial signals from a body, and a second cord with electrodes arranged for receiving limb signals from the body, as in the prior art.

In another arrangement in accordance with the invention, a first cord has leads for electrodes for the right and left legs, a second cord has leads for electrodes for signals from the two arms; and a third cord has leads for electrodes for signals from the chest (V1 to V6), for a total of three cords.

In these so-called EKG modes, the apparatus is capable of performing a twelve lead EKG with all of the corresponding data recorded simultaneously. In this second mode, external electrodes (such as silver chloride) are placed at the desired location and the device will record the current traveling through the heart after making the appropriate (ten-points) connections. The device utilizes its concealed two cords electrode system that augments the four limbs leads with the precordial or unipolar leads (undertaking the task from the left and right side of the body respectively).

The apparatus in accordance with the invention can be thought of as a still photo camera, that takes individual picture of the heart from one view (that corresponds to V1 through V6) and serial automatic pictures from two perspectives that correspond to: Lead I and aVL together; lead III and aVR; and lead II and aVF and so on. The first scenario is accomplished by generating a positive electrode within the diaphragm region in order to register a precordial, unipolar EKG tracing. A "snap shot" is taken of the heart's electrical activity utilizing the positive electrode at these various stages (V1-V6), which are perpendicular to the frontal plane (with respect to the heart's electrical current). This process is conveniently accomplished simultaneously while listening to the heart. Physiologically the electrical impulse from the heart travels anterior towards the chest wall and disseminate throughout the body. By convention it is practical to register an electrical signal traveling perpendicular to the heart by placing a positive electrode in its vicinity (as is done with a standardized twelve-lead EKG apparatus; registering the precordial leads from the chest wall).

Obtaining signals corresponding to the other six standardized leads for an EKG requires the usage of the limbs, namely the left arm, left foot and right arm to measure a current differential. The leads here are referred to as bipolar or augmented leads when used to execute this task. The right leg is commonly used as a common 'ground' for the EKG reading. For the purpose and function of the apparatus in accordance with the invention, a 'ground' can be created within or on the apparatus itself or a lead (not shown) situated in the body 14 can be appropriately placed and utilized, if and when the need arise. The invention is advantageously designed to register this phenomenon with very little adjustment.

Similarly to a conventional EKG machines, the apparatus in accordance with the invention utilizes a similar approach to electronically change the direction of the current and electrons to create the desire vectors to obtain its limb leads EKG tracing. As stated before, the device has three exposed electrodes, which can be used to make contact with the three limbs in an alert and cooperating patient.

The invention utilizes both traditional and wireless sound detection methods. A microphone and or a Doppler transducer is situated in the area of the diaphragm while the receiver component is situated near the earpieces. A common central processing unit allows for the discrimination of the received sound and also allows for modification and adjustment. The stethoscope is designed with a hollow connecting conduit tube that originates from the inner part of the diaphragms and terminates at the earpieces. This natural sound is totally independent of any electronics-electrical power and preserves the natural quality of sound detectable from a hollow structure or cavity such as the heart, lung and abdomen. In the very unlikely event of lack of power/electricity, the device would still be useful for its basic function.

Figure 9:
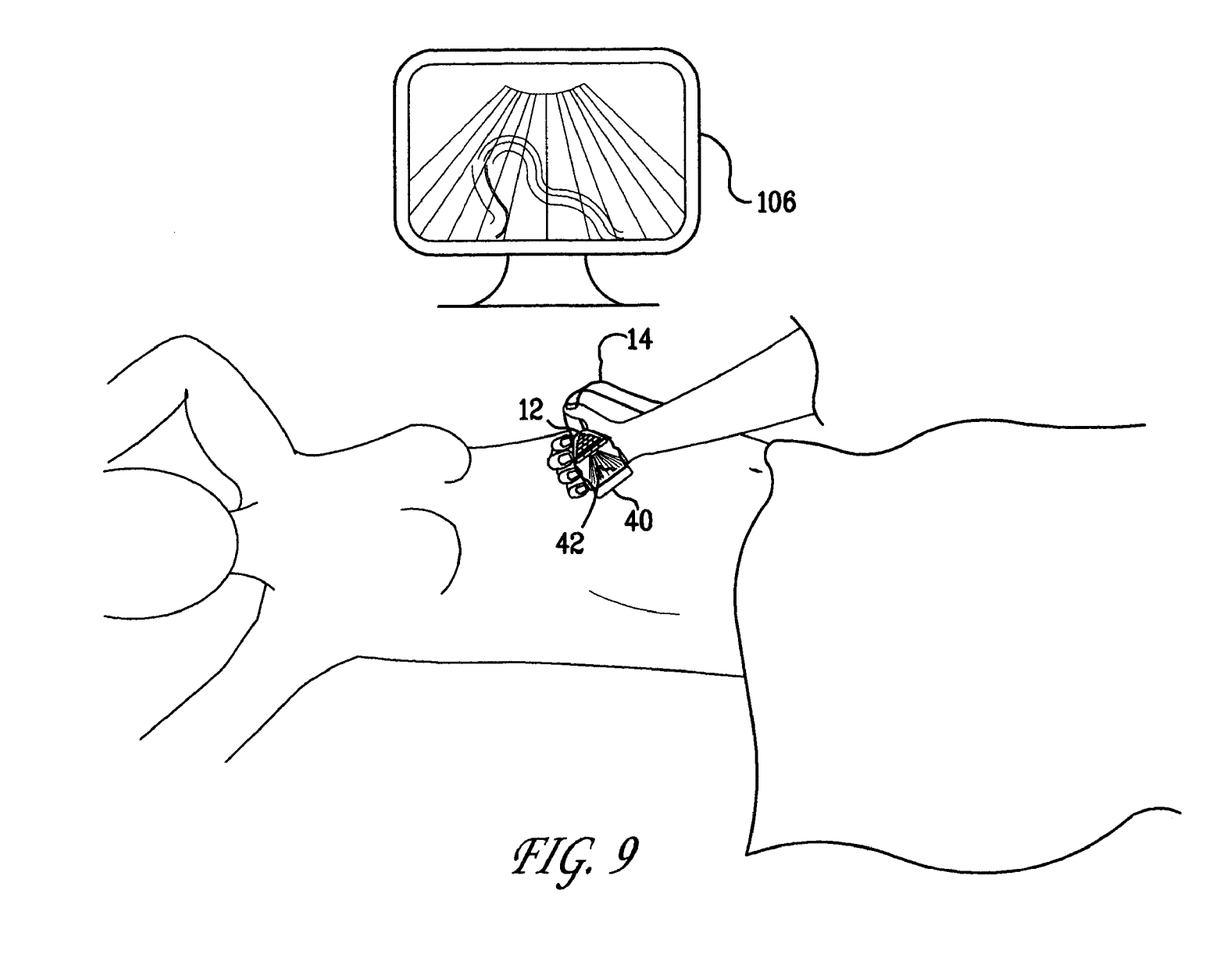
FIG. 9 illustrates use of the invention to produce a sonogram.

In FIG. 9, the apparatus 10 in accordance with the invention is being used on a human subject to investigate an area of concern within the abdominal cavity, by means of ultrasonic transducer 40 (FIG. 2), in a manner well know in the art. The portion 16 having the earpiece assembly 18 may be removed for hygienic reasons. When portion 16 is removed, the communications module 89 (FIG. 5) is activated, and broadband wireless signals may be transmitted to a portable multimedia monitor 106 or to a nearby terminal including a large data storage facility or printing capability or for simultaneous viewing for the display of data (which may also be on the smaller screen 42 of head 12). Also, acoustic data may be transmitted to portion 16 for listening with earpiece assembly 18.

Figure 10:
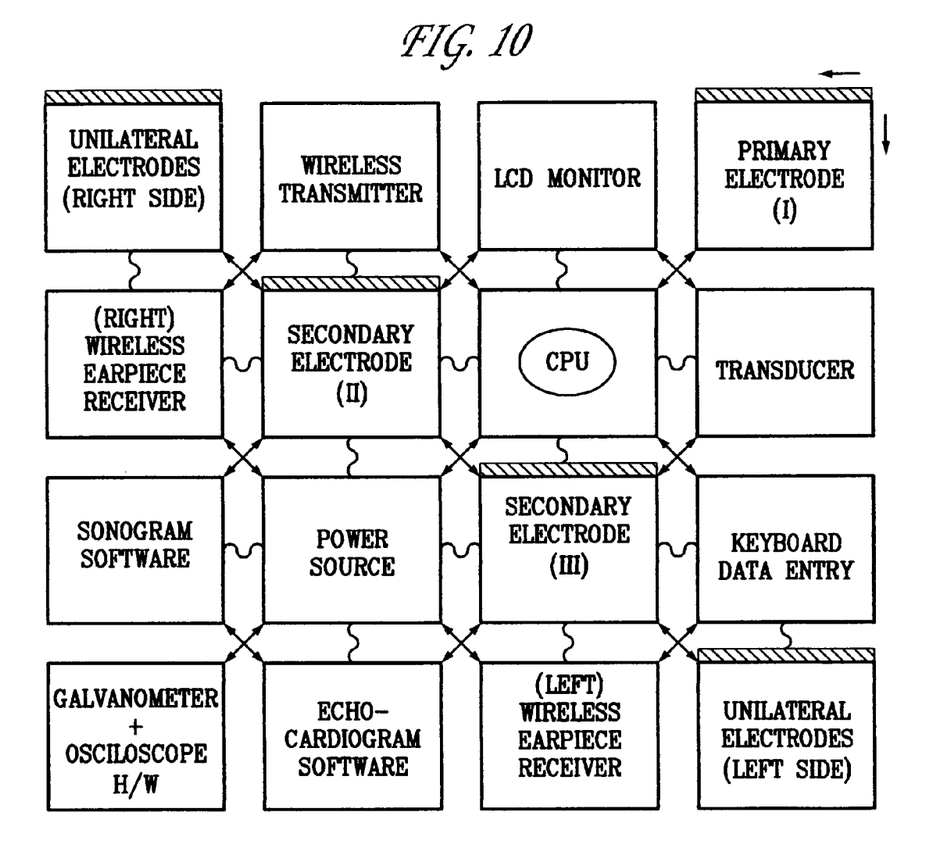
FIG. 10 is a conceptual block diagram of an apparatus in accordance with the invention.

FIG. 10 is a grid arrangement highlighting the major components of apparatus 10 and the interactions between them. The grid may be followed in a diagonal direction to best illustrate certain of these arrangements and interactions. All the sub units are intricately connected within the device and there is an established communication link between the device and an external receiving station that will serve the purpose to print/display larger images, process and store data, etc.

There are many other additional technical details that may be included which will occur to those skilled in the art after reading the present description. For example, the head 12 may be removeably connected to the body 14 so that they can be separately replaced or serviced, if necessary. Further, a rechargeable battery may be placed in housing 26 (FIG. 2) or in body 14 to provide electrical energy for powering the various electrical components of apparatus 10. The ultrasonic transducer 40 may operate in any one of several modes including A scan, B scan, Doppler or so called "M" mode. Digital communication with the communication modules 89 and 98 may be compatible with all digital forms of data transmission, display and analysis. The option of downloading the images to a mainframe computer/printer with interconnecting digital ports is available. Also the wireless transfer of data either by phone wires, cable wires, satellite signals or broadband network such as UWB, Bluetooth, Wi-Fi, WiMax, EDGE or 3G are all possible. While the apparatus has been described with a stethoscope portion with acoustic functions and pathways, it will be understood that an electronic stethoscope having a sound/vibration sensor or transducer for providing an electrical signal to amplify, and earpieces responsive to the amplified signal for producing sound for diagnostic or monitoring purposes, may also be used. Finally, one or more microprocessors may be included to process and store data.

The apparatus in accordance with the invention provides the following advantages:

1. All of the benefits of an EKG and sonogram and a diagnostic light source or sources are brought to the "finger tips" of a clinician.
2. Precious time needed to provide an EKG is reduced from hours to virtually seconds.
3. Lives can be saved and abnormalities in the heart can be detected upon an initial encounter.
4. The delivery of life saving care to patients is expedited.
5. Human resources needed to perform sonogram and EKG studies are conserved.
6. The bulky machine and cumbersome, often tangled wires associated with a twelve lead study are eliminated.
7. An excellent and inexpensive screening and diagnostic tool for the chest and abdomen are provided.
8. The most ubiquitous and some would say the most indispensable medical tool (the stethoscope) is modernized and enhanced.
9. Cardiac examination protocols may be revolutionized.
10. Doctors and medical personnel are given the confidence to do more with one comprehensive device.
11. The evolution of one multipurpose vital body-scanner tool has begun.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An apparatus for determining a condition of a living body, comprising:
   a first portion for acquiring acoustic signals from said body, said first portion having electrodes for acquiring electric signals from said body;
   a second portion comprising an elongate housing having acoustic conduits for conducting acoustic signals from said first portion to a third portion, wherein said third portion comprises a headset for listening to said acoustic signals, said third portion being removeably connectable to said second portion; and
   said third portion comprising at least one electrode for receiving electrical signals from said body, wherein said second portion further comprises electrical conductors for conveying electrical signals received by said at least one electrode of said third portion to said first portion.

2. The apparatus of claim 1, wherein said third portion is releaseably connected to said second portion, further comprising a communication link between said second portion and said third portion for transferring signals when said third portion is not connected to said second portion.

3. The apparatus of claim 2, wherein said communication link is a broadband communications link.

4. The apparatus of claim 2, wherein said communication link is a wireless communication link.

5. The apparatus of claim 1, wherein said first portion further comprises a display for providing a visual indication representative of at least one of said signals.

6. The apparatus of claim 5, in combination with an external display coupled to said apparatus with a broadband wireless real-time connection so that said external display wirelessly receives at least one of the acoustic signals and the electrical signals.

7. The apparatus of claim 1, wherein said first portion further comprises an ultrasonic transducer usable for performing an ultrasonic examination of at least a portion of said body.

8. The apparatus of claim 7, in combination with an external display coupled to said apparatus with a broadband wireless real-time connection so that said external display wirelessly receives at least one of the acoustic signals, the electrical signals, and signals acquired by said ultrasonic transducer.

9. The apparatus of claim 1, wherein said second portion is configured with an elongate cavity.

10. The apparatus of claim 9, further comprising at least one cover for covering said cavity.

11. The apparatus of claim 10, wherein said cover comprises at least one door swingably mounted to said second portion so that said at least one door swings away from said cavity to expose said cavity.

12. The apparatus of claim 9, further comprising a plurality of cords extending from said second portion, said cords each having a bundle of wires, each wire being configured at its end for an electrode for acquiring an electrical signal from said body, said cords being capable of bending and folding so as to fit within said cavity.

13. The apparatus of claim 12, wherein said cords and said wires are configured to place said electrodes for receiving electrocardiogram signals.

14. The apparatus of claim 12, wherein said plurality includes two cords, a first of said cords being configured so that respective electrodes associated with said first cord receive signals from a first side of the body, and a second of said cords being configured so that respective electrodes associated with said second cord receive signals from a second side of the body.

15. The apparatus of claim 14, wherein said first and second sides are left and right sides of said body.

16. The apparatus of claim 12, wherein said plurality includes two cords, a first of said cords being configured so that respective electrodes associated with said first cord receive precordial signals from the body, and a second of said cords being configured so that respective electrodes associated with said second cord receive limb signals from the body.

17. The apparatus of claim 12, wherein said plurality comprises three cords, a first of said cords having associated electrodes for receiving signals from both arms of the body, a second of said cords having associated electrodes for receiving precordial signals, and a third one of said cords having associated electrodes for receiving signals from both legs of the body.

18. The apparatus of claim 1, further comprising at least one adjustable light source on said first portion.

19. The apparatus of claim 1, wherein said first portion comprises a diaphragm having a first part and a second part, and said headset comprises a first earpiece and a second earpiece, said first part of said diaphragm providing signals for said first earpiece, and said second part of said diaphragm providing signals for said second earpiece.

20. The apparatus of claim 1, wherein said first portion is releasably connected to said second portion, and said second portion is releasably connected to said third portion.

21. A method for obtaining an electrocardiogram, utilizing the apparatus of claim 1.

22. An apparatus for determining a condition of a living body, comprising:
a first portion for acquiring acoustic signals from said body, said first portion having electrodes for acquiring electrical signals from said body;
a second portion comprising an elongate housing having acoustic conduits for conducting acoustic signals from said first portion to a third portion, wherein said third portion comprises a headset for listening to said acoustic signals, said third portion being removeably connectable to said second portion;
said second portion comprising at least one electrode for receiving electrical signals from said body; and
said third portion comprising at least one electrode for receiving electrical signals from said body, wherein said second portion further comprises electrical conductors for conveying electrical signals received by said at least one electrode of said second portion to said first portion and for conveying electrical signals received by said at least one electrode of said third portion to said first portion.

23. The apparatus of claim 22, wherein said at least one electrode of said second portion comprises a plurality of cords, said cords each having a bundle of wires, each wire being configured at its end for an electrode for acquiring an electrical signal from said body, a first of said cords being configured so that respective electrodes associated with said first cord receive signals from a first side of the body, and a second of said cords being configured so that respective electrodes associated with said second cord receive signals from a second side of the body.

24. The apparatus of claim 22, wherein said at least one electrode of the second portion comprises a plurality of cords, said cords each having a bundle of wires, each wire being configured at its end for an electrode for acquiring an electrical signal from said body, wherein said plurality comprises three cords, a first of said cords having associated electrodes for receiving signals from both arms, a second of said cords having associated electrodes for receiving precordial signals, and a third one of said cords having associated electrodes for receiving signals from both legs of the body.

25. An apparatus for determining a condition of a living body, comprising:
a first portion for acquiring acoustic signals from said body, said first portion having electrodes for acquiring electric signals from said body;
a second portion comprising an elongate housing having acoustic conduits for conducting acoustic signals from said first portion to a third portion wherein said third portion comprises a headset for listening to said acoustic signals; and wherein said third portion is removeably connectable to said second portion; and
wherein said second portion is configured with an elongate cavity, and at least one cover for covering said cavity, said cover comprising at least one door swingably mounted to said second portion so that said at least one door swings away from said cavity to expose said cavity.

26. A system for determining a condition of a living body, comprising:
an apparatus comprising:
a first portion for acquiring acoustic and electrical signals from said body, said first potion having electrodes for acquiring the electric signals and wherein said first portion further comprises an ultrasonic transducer for performing an ultrasonic examination of at least a portion of said body;
a second portion comprising an elongate housing having acoustic conduits for conducting acoustic signals from said first portion to a third portion, wherein said third portion comprises a headset for listening to said acoustic signals, said third portion being removeably connectable to said second portion; and
said third portion comprising at least one electrode for receiving electrical signals from the body, wherein said second portion further comprises electrical conductors for conveying electrical signals received by said at least one electrode of said third portion to said first portion; and
an external display wirelessly coupled to said apparatus by a broadband wireless real-time connection so that said external display wirelessly receives at least one of the acoustic signals, the electrical signals, and signals acquired by said ultrasonic transducer.

27. The system of claim 26, wherein said first portion further comprises a display for providing a visual indication representative of at least one of said signals.

* * * * *